United States Patent
Braun et al.

(10) Patent No.: US 9,710,141 B2
(45) Date of Patent: Jul. 18, 2017

(54) METHOD FOR SELECTING A RECORDING AREA AND SYSTEM FOR SELECTING A RECORDING AREA

(71) Applicant: Siemens Aktiengesellschaft, München (DE)

(72) Inventors: Christoph Braun, Rosenheim (DE); Johann Uebler, Nuremberg (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 0 days.

(21) Appl. No.: 14/867,291

(22) Filed: Sep. 28, 2015

(65) Prior Publication Data
US 2016/0092078 A1    Mar. 31, 2016

(30) Foreign Application Priority Data
Sep. 29, 2014  (DE) ........................ 10 2014 219 667

(51) Int. Cl.
*G06K 9/00*    (2006.01)
*G06F 3/0484*    (2013.01)
(Continued)

(52) U.S. Cl.
CPC ............ *G06F 3/04842* (2013.01); *A61B 6/03* (2013.01); *A61B 6/032* (2013.01); *A61B 6/04* (2013.01);
(Continued)

(58) Field of Classification Search
CPC ................ G06K 9/00; A61B 6/00; G06F 3/00
(Continued)

(56) References Cited

U.S. PATENT DOCUMENTS 8,577,444 B2 * 11/2013 Klingenbeck-Regn .. A61B 6/12
                                                                600/424
9,539,441 B2 *  1/2017 Lane .................... A61N 5/1039
(Continued)

FOREIGN PATENT DOCUMENTS

DE    10109219 A1    9/2002
DE    10210050 A1    12/2003
(Continued)

OTHER PUBLICATIONS

Sedlmaier Martin et al., "Kontaktlose Oberflächenvermessung zur Topogramm-Optimierung" ; 2013.
German Office Action dated Jul. 3, 2015.

*Primary Examiner* — Abolfazl Tabatabai
(74) *Attorney, Agent, or Firm* — Harness, Dickey & Pierce, P.L.C.

(57) ABSTRACT

In a 3D image of a patient supported on a patient table, the 3D image incorporates depth information about the outline of the patient. The 3D image is received and image information based on the 3D image is displayed on a screen, embedded into a graphical user interface. A first recording area is selectable particularly precisely by the selection being based on the inputting of a first start position and also a first end position in the displayed image information via the graphical user interface. The first recording area is displayed as a graphically highlighted first zone. Furthermore, a first position of the first recording area is determined relative to a recording unit based on the depth information and also based on the selection of the first recording area. This results in the first position being determined rapidly and particularly reliably, in particular in the vertical direction.

31 Claims, 4 Drawing Sheets

(51) Int. Cl.
*A61B 6/03* (2006.01)
*A61B 6/04* (2006.01)
*A61B 34/00* (2016.01)
*G06F 3/0488* (2013.01)
*G06K 9/20* (2006.01)
*G06K 9/66* (2006.01)
*G06T 7/00* (2017.01)
*G06T 11/00* (2006.01)
*A61B 6/00* (2006.01)
*H04N 13/02* (2006.01)
*H05G 1/28* (2006.01)

(52) U.S. Cl.
CPC ............ *A61B 6/0407* (2013.01); *A61B 6/545* (2013.01); *A61B 34/00* (2016.02); *G06F 3/0488* (2013.01); *G06K 9/2081* (2013.01); *G06K 9/66* (2013.01); *G06T 7/0012* (2013.01); *G06T 11/003* (2013.01); *A61B 6/0457* (2013.01); *G06K 2209/05* (2013.01); *G06T 2200/04* (2013.01); *G06T 2200/24* (2013.01)

(58) Field of Classification Search
USPC .... 382/128–134; 378/4, 8, 21–27, 901, 162; 600/407, 410, 411, 425, 427; 348/46
See application file for complete search history.

(56) References Cited

U.S. PATENT DOCUMENTS

| | | |
|---|---|---|
| 2002/0118280 A1 | 8/2002 | Medlar et al. |
| 2003/0225325 A1 | 12/2003 | Kagermeier et al. |
| 2004/0081341 A1 | 4/2004 | Cherek et al. |
| 2004/0082852 A1 | 4/2004 | Cherek et al. |
| 2007/0172102 A1 | 7/2007 | Hempel |
| 2008/0292048 A1 | 11/2008 | Haras et al. |
| 2009/0285357 A1 | 11/2009 | Khamene |
| 2012/0209106 A1* | 8/2012 | Liang .................. A61B 5/7425 600/414 |
| 2013/0083894 A1 | 4/2013 | Niebler et al. |
| 2015/0104092 A1 | 4/2015 | Flohr et al. |

FOREIGN PATENT DOCUMENTS

| | | |
|---|---|---|
| DE | 10232481 A1 | 1/2004 |
| DE | 10232676 A1 | 1/2004 |
| DE | 102006001850 A1 | 8/2007 |
| DE | 102007024452 A1 | 11/2008 |
| DE | 102007017794 B3 | 12/2008 |
| DE | 102011083876 A1 | 4/2013 |
| DE | 102012201798 A1 | 8/2013 |
| DE | 102012214513 A1 | 2/2014 |
| DE | 102013220665 A1 | 4/2015 |

* cited by examiner

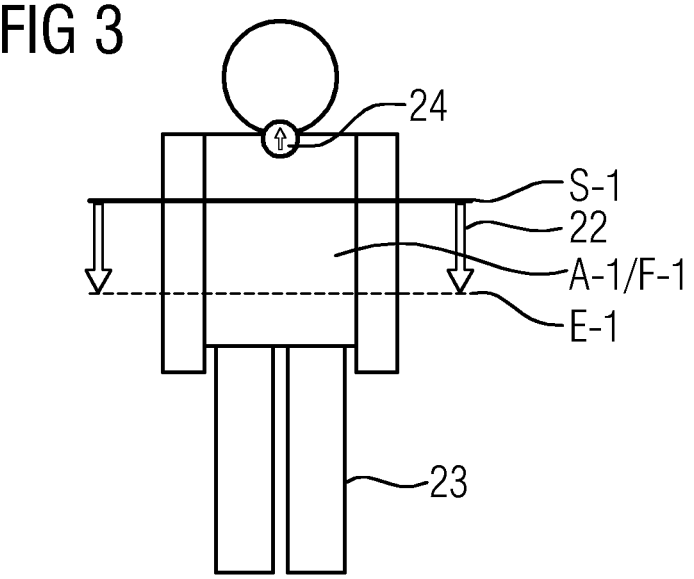
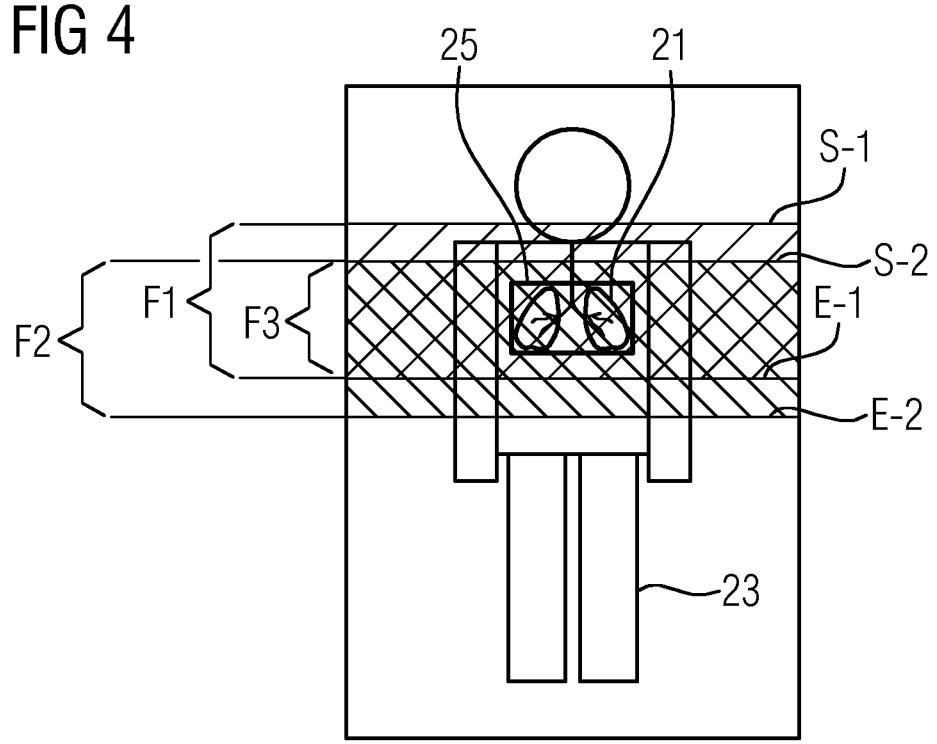

METHOD FOR SELECTING A RECORDING AREA AND SYSTEM FOR SELECTING A RECORDING AREA

PRIORITY STATEMENT

The present application hereby claims priority under 35 U.S.C. §119 to German patent application number DE 102014219667.1 filed Sep. 29, 2014, the entire contents of which are hereby incorporated herein by reference.

FIELD

At least one embodiment of the invention generally relates to a method for selecting a recording area and/or a system for selecting a recording area.

BACKGROUND

Tomography is an imaging method in which cross-sectional images of a three-dimensional recording area are reconstructed. A tomography machine has a recording unit with a central system axis. The recording unit can be realized in the form of a ring or a tunnel. The recording unit furthermore has an isocenter in which the conditions for a tomographic recording are particularly advantageous. Typically, the system axis and the isocenter are caused to overlap at least partly. The recording area can be traversed along the system axis and therefore through the isocenter during the tomographic recording. At the end of the tomographic recording, the projections are processed such that a tomographic image is created.

In the case of X-ray tomography, X-ray projections are recorded at various projection angles. In this respect, the recording unit rotates together with a radiation source and also a radiation detector around the system axis and also around the recording area. The point of intersection between the beams emitted by the radiation source and the system axis forms the isocenter of the recording unit. In the case of magnetic resonance tomography, in particular, the radiation detector can be arranged in the form of local coils outside the recording unit. Furthermore, the system axis is arranged parallel to a main magnetic field in the case of magnetic resonance tomography, with the isocenter being characterized by a particularly homogeneous main magnetic field.

A decisive factor for the quality of a tomographic image of this type is how the recording area of the subject is positioned. As a rule it is desirable, for example, to position the radiological central point of the recording area, or an examination area situated within the recording area, in the isocenter of the recording unit of a tomography machine. As a result, attenuation of the radiation takes place as evenly as possible. Precise positioning is important in the clinical environment in particular if the recording area involves a bodily region of a patient. This is because a repeat tomographic recording due to incorrect positioning goes hand in hand with an additional dose exposure and also a considerable time delay in routine clinical activities. Furthermore, the highest possible quality of the tomographic image is indispensable in clinical diagnostics.

The positioning of the patient is traditionally carried out by an operator traversing the patient table manually. Furthermore, the operator uses an optical marking, which is projected on to the patient, typically in the form of a laser line, for the positioning. The patient's positioning perpendicular to the system axis is particularly problematic in this respect, in particular the positioning in the vertical direction.

Due to the high level of time pressure in routine clinical activities, the patient's vertical position in particular is frequently set with insufficient precision.

SUMMARY

An embodiment of the present invention enables precise selection of a recording area for rapid and reliable positioning of a patient.

An embodiment of the present invention is directed to a method. An embodiment of the present invention is directed to a system.

Features, advantages, and alternative embodiments mentioned in this respect are also to be applied in like manner to the other claimed subject matters and vice versa. In other words, the subject matter claims (which are directed toward a system for example) can also be developed together with the features that are described or claimed in connection with a method. In this respect, the corresponding functional features of the method are realized by way of corresponding subject-matter modules.

An embodiment of the invention is based on a 3D image of a patient supported on a patient table, wherein the 3D image incorporates depth information about the outline of the patient. A 3D image of this type is received and image information based on the 3D image is displayed on a screen, wherein the image information is embedded into a graphical user interface.

The inventors have recognized that a first recording area can be selected particularly precisely if the selection is based on the inputting of a first start position and also a first end position in the displayed image information via the graphical user interface, wherein the first recording area is displayed as a graphically highlighted first zone. This is because by inputting the first start position and also the first end position, the first recording area can be selected as desired.

At least one embodiment of the inventive display of the zone also facilitates monitoring of the selection. Furthermore, a first position of the first recording area is determined relative to a recording unit based on the depth information and also based on the selection of the first recording area. This results in the first position being determined rapidly and particularly reliably, in particular in the vertical direction. Such rapid and reliable positioning is not possible as a rule in the case of traditional manual positioning.

At least one embodiment is directed to a method for selecting a recording area, comprising:
  Receiving (REC) a 3D image of a patient (3) supported on a patient table (6), wherein the 3D image incorporates depth information about the outline of the patient (3),
  Displaying (SCR) image information based on the 3D image on a screen (11), wherein the image information is embedded into a graphical user interface,
  Selecting (SEL) a first recording area (A-1) based on the inputting of a first start position (S-1) and also a first end position (E-1) in the displayed image information by way of the graphical user interface, wherein the first recording area (A-1) is displayed as a graphically highlighted first zone (F-1),
  Determining (CAL) a first position (P-1) of the first recording area (A-1) relative to a recording unit (17) based on the depth information and also based on the selection of the first recording area (A-1).

Furthermore, at least one embodiment of the invention relates to a system, comprising:

an interface for receiving a 3D image of a patient supported on the patient table, wherein the 3D image incorporates depth information about the outline of the patient, a screen for displaying image information based on the 3D image, wherein the image information is embedded into a graphical user interface, an input unit for selecting a first recording area based on the inputting of a first start position and also a first end position in the displayed image information via the graphical user interface, wherein the first recording area is displayed as a graphically highlighted first zone, and an arithmetic unit for determining a first position of the first recording area relative to a recording unit based on the depth information and also based on the selection of the first recording area.

An embodiment of the invention furthermore relates to a system with a tomography machine, which furthermore comprises:

a recording unit with a central system axis, a patient table capable of being moved along the system axis, a radiation source and a radiation detector operating in conjunction with the radiation source, and a control unit for automatic positioning of the first recording area in the first position by moving the patient table relative to the recording unit, wherein the tomography machine is designed for a first tomographic recording of the first recording area in the first position.

BRIEF DESCRIPTION OF THE DRAWINGS

The invention is described in detail and explained below by reference to the example embodiments represented in the figures.

These show the following:

FIG. 3 A screen view with a first recording area in plan view,

FIG. 4 A screen view with a first and also a second recording area in plan view, FIG. 5 A screen view with a first and also a second recording area in side view, FIG. 6 A scalable patient model, FIG. 7 A flow diagram for a method for automatic patient positioning.

DETAILED DESCRIPTION OF THE EXAMPLE EMBODIMENTS

Figure 1:
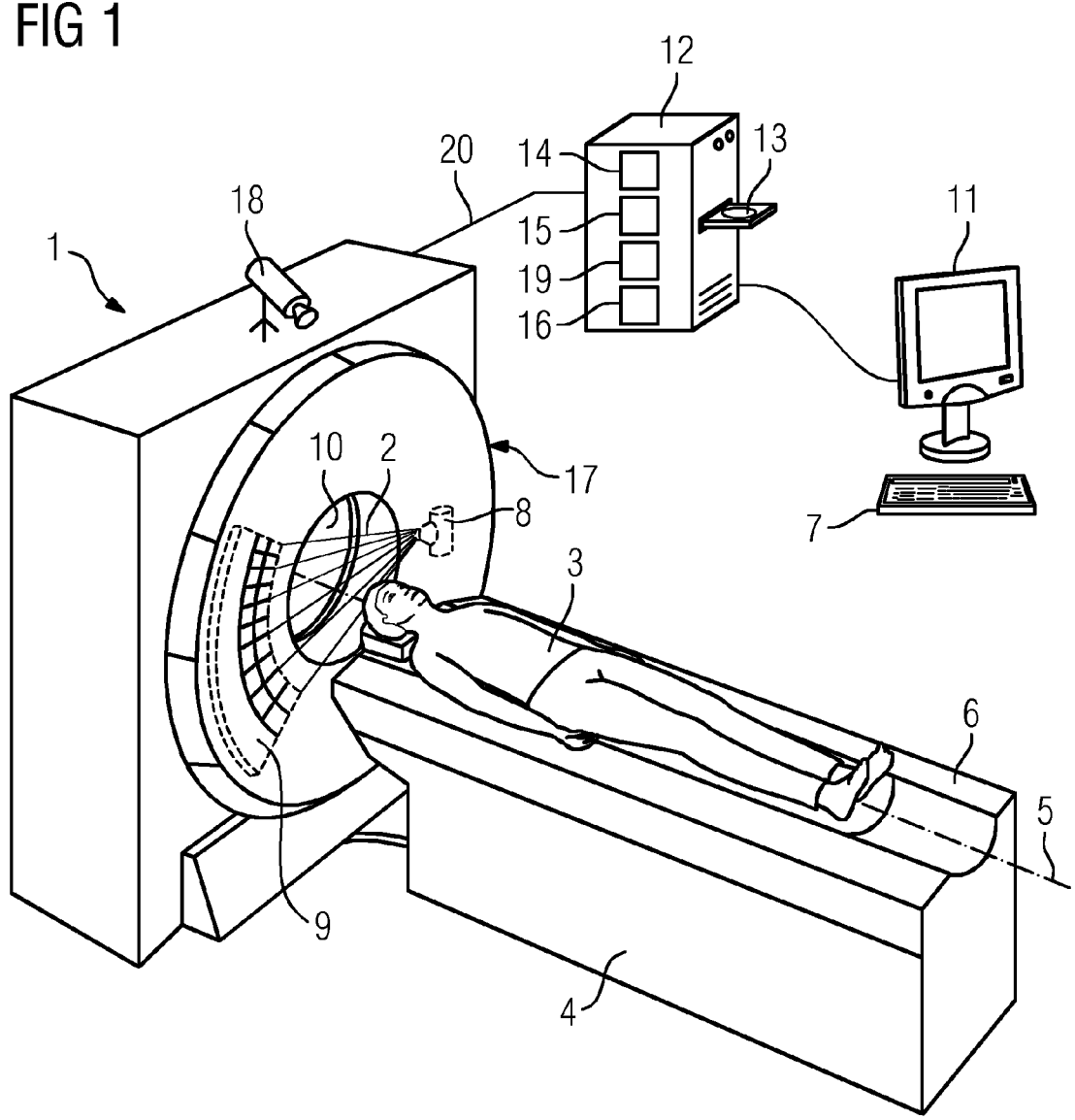
FIG. 1 A system for selecting a recording area.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Further, although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

An embodiment of the invention is based on a 3D image of a patient supported on a patient table, wherein the 3D image incorporates depth information about the outline of the patient. A 3D image of this type is received and image information based on the 3D image is displayed on a screen, wherein the image information is embedded into a graphical user interface.

The inventors have recognized that a first recording area can be selected particularly precisely if the selection is based on the inputting of a first start position and also a first end position in the displayed image information via the graphical user interface, wherein the first recording area is displayed as a graphically highlighted first zone. This is because by inputting the first start position and also the first end position, the first recording area can be selected as desired.

At least one embodiment of the inventive display of the zone also facilitates monitoring of the selection. Furthermore, a first position of the first recording area is determined relative to a recording unit based on the depth information and also based on the selection of the first recording area. This results in the first position being determined rapidly and particularly reliably, in particular in the vertical direction. Such rapid and reliable positioning is not possible as a rule in the case of traditional manual positioning.

According to a further embodiment of the invention, the first start position and also the first end position are selected independently of each other. As a result, the first and also the second recording area can be selected particularly flexibly. In particular, neither a fixed length of the recording area nor a fixed orientation of the recording direction are predefined.

According to a further embodiment of the invention, a recording direction for the first recording area is displayed symbolically in the graphical user interface, wherein the recording direction is defined by the relative orientation of the first start position and also the first end position. This results in tomographic recordings with an incorrect orientation being prevented so that there is a higher level of certainty during the planning of tomographic recordings.

According to a further embodiment of the invention, at least one examination area is marked in the image information. As a result, the selection of a recording area can be simplified. The marking can be carried out both actively by the interaction of an operator with the image information and also by calling up stored prior information. The marking can be based on a called-up recording protocol, for example. Furthermore, the marking can be based on a recording area that is already selected, in order to mark an examination area within a recording area, for example.

According to a further embodiment of the invention, the determining is furthermore based on an item of information about the radiation absorption of the first recording area, wherein the first position specifies a radiological central point of the first recording area, or of the examination area within the first recording area, such that the radiological central point is situated in the isocenter of the recording unit. This aspect refers to a particularly important application of an embodiment of the invention. This is because if the radiological central point is situated in the isocenter, then the resulting image impression of a tomographic recording is particularly homogeneous. In this respect, the radiological central point can refer in particular to a radiological central point averaged along the system axis.

According to a further embodiment of the invention, the information about the radiation absorption incorporates a scalable patient model with various sub-areas, wherein the patient model is based on the 3D image and in particular the depth information, wherein the patient model is furthermore based on generic radiation absorption properties of the sub-areas. As a result, the radiological central point can be accurately determined with a particularly low use of radiation, and in particular without prior recording of an X-ray image.

According to a further embodiment of the invention, the first position specifies a geometric central point of the first recording area or of the examination area such that the geometric central point is situated in the isocenter of the recording unit. A further particularly important application is involved in this respect. The geometric central point is frequently chosen in order to achieve the highest possible local resolution during a tomographic recording.

According to a further embodiment of the invention, a second recording area with a second start position and also a second end position is displayed in the image information, wherein the second recording area is displayed as a graphically highlighted second zone. As a result, it is particularly simple to compare the first recording area and the second recording area with each other, with the result that positioning can be carried out particularly rapidly and reliably. In particular, the second recording area can be used to correct the first recording area.

According to a further embodiment of the invention, the second recording area is defined by way of the examination area, wherein the examination area is selected by calling up a stored recording protocol. As a result, the comparison of the first recording area with a second recording area defined by an examination protocol can take place particularly rapidly and reliably.

According to a further embodiment, the second recording area is defined by way of the examination area, wherein the examination area is selected by inputting a marking in the displayed image information via the graphical user interface. This results in the work flow being structured particularly flexibly.

According to a further embodiment of the invention, the second recording area is defined by way of the examination area, wherein the examination area is selected in the 3D image and/or in the image information by way of pattern recognition. This results in the work sequence being further speeded up and automated.

According to a further embodiment, a graphically highlighted third zone displays the area in which the first recording area and the second recording area overlap.

According to a further embodiment of the invention, the first recording area is compared with the second recording area, wherein a confirmation signal or a warning is displayed in the user interface on the basis of the comparison. The comparison allows various information about an optimal recording area to be taken into account and thereby ensures a particularly precise determination of the first position.

According to a further embodiment of the invention, the second recording area is displayed on the basis of the first start position, wherein the first start position and the second start position coincide. If only a first start position is input initially, therefore, then a second end position is suggested by the system. In this case, the first and/or second start position and also the second end position (and therefore the second recording area) form a suggestion for the first recording area.

According to a further embodiment of the invention, the inputting of the first end position incorporates the confirmation or relocation of the second end position so that the first end position constitutes the confirmed or relocated second end position. The suggestion for the first recording area can therefore be modified and then confirmed or confirmed directly without modification.

According to a further embodiment of the invention, anatomical landmarks in the 3D image and/or in the image information are identified by way of pattern recognition, and wherein the second recording area is defined on the basis of a learning algorithm, wherein the learning algorithm analyzes the first start position relative to the anatomical landmarks. A learning algorithm of this type makes it possible, in particular, to make particularly precise suggestions for a first recording area. Furthermore, the learning algorithm can analyze the relative position of a plurality of landmarks with respect to each other and/or relative to the first start position. The learning algorithm can also analyze the patient's bodily dimensions such as body height for example.

According to a further embodiment of the invention, the image information is displayed on a touch-sensitive screen, wherein selection is carried out by touching the touch-sensitive screen. The intuitive handling of a touch-sensitive screen results in a further speeding up of the work flow.

Furthermore, at least one embodiment of the invention relates to a system, comprising:
  an interface for receiving a 3D image of a patient supported on the patient table, wherein the 3D image incorporates depth information about the outline of the patient,
  a screen for displaying image information based on the 3D image, wherein the image information is embedded into a graphical user interface,
  an input unit for selecting a first recording area based on the inputting of a first start position and also a first end position in the displayed image information via the graphical user interface, wherein the first recording area is displayed as a graphically highlighted first zone, and
  an arithmetic unit for determining a first position of the first recording area relative to a recording unit based on the depth information and also based on the selection of the first recording area.

According to a variant embodiment of the invention, the system further incorporates a 3D camera, wherein the 3D camera is aligned toward the patient table. In particular, the 3D camera can be fixed to the tomography machine or centrally above the patient table, on a ceiling of the building for example.

According to a further variant embodiment, the screen and the input unit are together realized in the form of a touch-sensitive screen.

Additionally, the system described here and its variant embodiments can be designed according to the invention so as to implement various previously described aspects of at least one embodiment of the inventive method.

An embodiment of the invention furthermore relates to a system with a tomography machine, which furthermore comprises:

a recording unit with a central system axis, a patient table capable of being moved along the system axis, a radiation source and a radiation detector operating in conjunction with the radiation source, and a control unit for automatic positioning of the first recording area in the first position by moving the patient table relative to the recording unit, wherein the tomography machine is designed for a first tomographic recording of the first recording area in the first position.

A tomography machine can be a magnetic resonance tomography machine. In this case, the radiation incorporates a high-frequency alternating field in the radio frequency range. The radiation source in this case constitutes at least one coil for generating the high-frequency alternating field. The radiation detector in the case of magnetic resonance tomography involves at least one coil for detecting high-frequency radiation.

Furthermore, the tomography machine can be an X-ray machine which is designed for recording a plurality of X-ray projections from different projection angles. A tomography machine of this type involves, for example, a computed tomography machine with an annular rotary frame or a C-arm X-ray machine. The recordings can be generated during a rotary, and in particular continuous, movement of a recording unit with an X-ray source and an X-ray detector operating in conjunction with the X-ray source. In this respect, the X-ray source emits X-ray radiation within a fan-shaped or conical area. The X-ray source can be, in particular, an X-ray tube with a rotary anode. The X-ray detector involves, for example, a line detector with a plurality of lines. However, the X-ray detector can also be realized as a flat detector.

With a tomography machine, it is possible to record both a tomographic image and also a topogram. A topogram is an overview recording of a patient which, in particular, can only be recorded at one projection angle by the recording unit.

The imaging system can have a reconstruction unit for reconstructing a tomographic image. Furthermore, the imaging system can have an arithmetic unit. Both the arithmetic unit and also the reconstruction unit can be realized both in the form of hardware and also software. For example, the arithmetic unit or the reconstruction unit is realized in the form of a so-called FPGA ("Field Programmable Gate Array") or incorporates an arithmetic logic unit.

A 3D image incorporates a spatially two-dimensional image, or 2D image for short, wherein depth information is assigned to the individual pixels in the 2D image. This depth information therefore displays information in a third spatial dimension. A 3D camera is suitable for recording 3D images of this type. The 3D camera is designed for detecting electromagnetic radiation, and in particular for detecting electromagnetic radiation in a low-frequency spectral region—compared with X-ray radiation—such as in the visible or infrared spectral regions. The 3D camera is realized for example in the form of a stereo camera or as a propagation-time measurement system (referred to as a "time-of-flight camera"). By using structured illumination, the 3D camera can also be designed so as to record a 3D image.

To receive the 3D image, use is made of an interface. The interface involves generally familiar hardware or software interfaces such as the PCI bus, USB or Firewire hardware interfaces.

Image information based on a 3D image of a patient can be displayed on a screen. The display can take place such that the patient is displayed with a predefinable perspective, for example front or side. A perspective of this type can be based in particular on the transformation of the 3D image. Furthermore, the image information based on the 3D image can display not just the patient directly, but an avatar adjusted to the patient. An avatar is a scalable patient model. For example, the patient model can involve the outline of a representation of a person or the outline of individual parts of a person's body. For example, bodily properties such as height, diameter of thorax, and shoulder width can be adjusted by scaling the patient model. Bodily properties of this type can be ascertained from the 3D image by way of methods, in particular automatic methods, of image processing.

The selection of a recording area can take place by way of separate input of a start position and also an end position in the displayed image information. The recording area fills the area between the start position and the end position and is therefore delimited by the start position and the end position. The start position and also the end position can be displayed symbolically in each case, in particular by way of a line. But selection can also be carried out by placing a zone in the image information, wherein the zone corresponds to the recording area. A recording area can be highlighted by a color value and/or brightness value that diverges from the surroundings.

The screen can be an LCD, plasma or OLED screen, for example. Furthermore, it can be a touch-sensitive screen that is also realized in the form of an input unit. A touch-sensitive screen of this type can be integrated into the tomography machine, for example in a gantry, or be realized as part of a mobile device. Alternatively, the input unit can be realized in the form of a keyboard, mouse, microphone for voice input or in some other manner.

According to an embodiment of the invention, the determination of a position is based on depth information and also a selected recording area. The position relates in particular to the plane perpendicular to the system axis of the recording unit. In specific embodiments of the invention, the position means the vertical position. The determination of the position can be based in particular on a volume of the recording area calculated from the 3D image and/or a surface area of the recording area calculated from the 3D image.

Furthermore, the position can be determined on the basis of a density distribution or a distribution of radiation absorption properties within a volume and/or surface area of this type. A plurality of positions can be calculated for sub-areas of the recording area, and in particular the sub-areas can be layers along the system axis. A position in the isocenter can therefore refer to a position for a layer of the patient situated in the course of the beam. Furthermore, a specific position in the image information can be shown as a point, zone or line for example.

A control unit is used for positioning. The control unit can be realized both in the form of hardware and also software. In particular, the control unit can include a device for calculating and also for transmitting a control signal so that the control unit exerts control over the movement of the patient table with the aid of the control signal. It can be ensured, by way of corresponding calibration, that the relationship between the external coordinate system in which a recording area is situated and the internal coordinate system of the 3D camera (and a 3D image) is known to the control unit. The control unit generates the control signal such that the recording area appears at a specific position in the external coordinate system. The arithmetic unit or another unit of the imaging system is therefore designed so as to convert the position in a 3D image into a position in the external coordinate system by way of a coordinate transformation process.

With regard to automatic positioning, a specific position is sent by the arithmetic unit to a control unit, by using a position signal for example. In the context of the present application, "automatic" means that the respective step runs autonomously by using an arithmetic or control unit, and that essentially no interaction of an operator with the imaging system is necessary for the respective step. In other words, the arithmetic activity for steps such as automatic determination or automatic positioning is implemented by the arithmetic or control unit. At most, the operator has to confirm calculated results or implement interim steps.

In further embodiments of the invention with "fully automatically" implemented steps, no interaction at all by an operator is necessary for implementing these steps. Irrespective of whether the individual steps are implemented "automatically" or "fully automatically", the inventive method can form part of a work sequence that additionally does require the interaction of an operator. The interaction with the operator can consist in the said operator manually selecting a recording protocol and/or a clinical issue, from a menu presented by using a screen for example.

The arithmetic unit and also the control unit can furthermore be designed so as to implement certain method steps by being programmed so as to implement these method steps. In particular, the arithmetic unit and the control unit can each have a microprocessor that is programmed so as to implement the respective method steps.

The geometric central point is a point or an axis that specifies the geometric center of the recording area. In particular, the geometric center can be determined on the basis of a homogeneous density distribution of a calculated volume or a calculated surface area of the patient. The radiological central point is a point or an axis that specifies the center of the attenuation distribution of the recording area. In particular, the radiological central point can be determined on the basis of a non-homogeneous density distribution or a non-homogeneous distribution of radiation absorption properties of a calculated volume or a calculated surface area of the patient. For the purposes of the present application, radiation absorption also incorporates X-ray scattering. In particular, a specific density or a specific radiation absorption property can be assigned to a specific part or organ of the patient's body. A scalable patient model can incorporate an assignment of this type.

In this respect, the radiological or geometric central point can refer in particular to a radiological central point averaged along the system axis. In this respect, according to a variant, a property such as a density distribution or a radiation absorption property of a recording area can be averaged along the system axis initially in order then to determine the corresponding central point. In a further variant, a recording area is subdivided into sub-areas along the system axis and individual central points are determined for each of these sub-areas, which central points are then averaged.

FIG. 1 shows a system for selecting a recording area using the example of a computed tomography machine. The computed tomography machine shown here has a recording unit 17 incorporating a radiation source 8 in the form of an X-ray source, and also a radiation detector 9 in the form of an X-ray detector. During the recording of projections, the recording unit 17 rotates around an axis of rotation 5, and the X-ray source emits beams 2 in the form of X-rays during the recording. The X-ray source in the example shown here is an X-ray tube. The X-ray detector in the example shown here is a line detector with a plurality of lines.

In the example shown here, a patient 3 is lying on a patient table 6 during the recording of projections. The patient table 6 is connected to a table base 4 such that that the said base 4 supports the patient table 6 together with the patient 3. The patient table 6 is designed so as to move the patient 3 along a recording direction through the aperture 10 in the recording unit 17. The recording direction is dictated by the system axis 5 as a rule, around which axis the recording unit 17 rotates during the recording of X-ray projections. In the case of a spiral recording, the patient table 6 is moved continuously through the aperture 10 while the recording unit 17 rotates around the patient 3 and records X-ray projections. The X-rays therefore describe a spiral on the surface of the patient 3.

Furthermore, the system for selecting a recording area shown here has a 3D camera 18 which is designed with an interface 16 for receiving REC a 3D image recorded by the 3D camera 18. In the example shown here, the interface 16 is realized as part of the computer 12. The computer 12 is connected to an output unit in the form of a screen 11 and also an input unit 7. The screen 11 is designed for displaying SCR various image information based on the 3D image. In particular, a photographic picture 23 of the patient 3 or a patient model adjusted to the patient 3 can be displayed. The input unit 7 is designed for selecting SEL at least a first recording area A-1. The input unit 7 is a keyboard, a mouse, a so-called "touch-screen" or even a microphone for voice input, for example.

The determination CAL of at least one first position P-1 is carried out by using an arithmetic unit 15. The arithmetic unit 15 can incorporate a computer-readable medium 13 or operate in conjunction with the said medium. In the example shown here, a control unit 19 is integrated into the computer 12 and transmits a control signal 20 for positioning POS the patient table 6. The positioning signal 20 is transmitted, for example, to a motor for moving the patient table 6. The movement can take place both along the system axis 5, that is to say horizontally, and also perpendicular to the system axis 5, in particular vertically. The movements of the patient table 6 in different spatial directions can take place independently of each other in this respect.

The tomography machine can access stored recording protocols that are capable of being called up. In particular, the tomography machine can have its own working memory into which a recording protocol can be loaded. In specific embodiments of the invention, the recording protocol can be used for selecting SEL the first recording area A-1 or the second recording area A-2, for selecting SEL an examination area 21, and/or for determining CAL the first position P-1. After or during a first tomographic recording TOM-1, a tomographic image can be reconstructed on the basis of the recorded projections. For the purpose of reconstructing a tomographic image, the system shown here furthermore has a reconstruction unit 14, designed so as to reconstruct a tomographic image.

Figure 2:
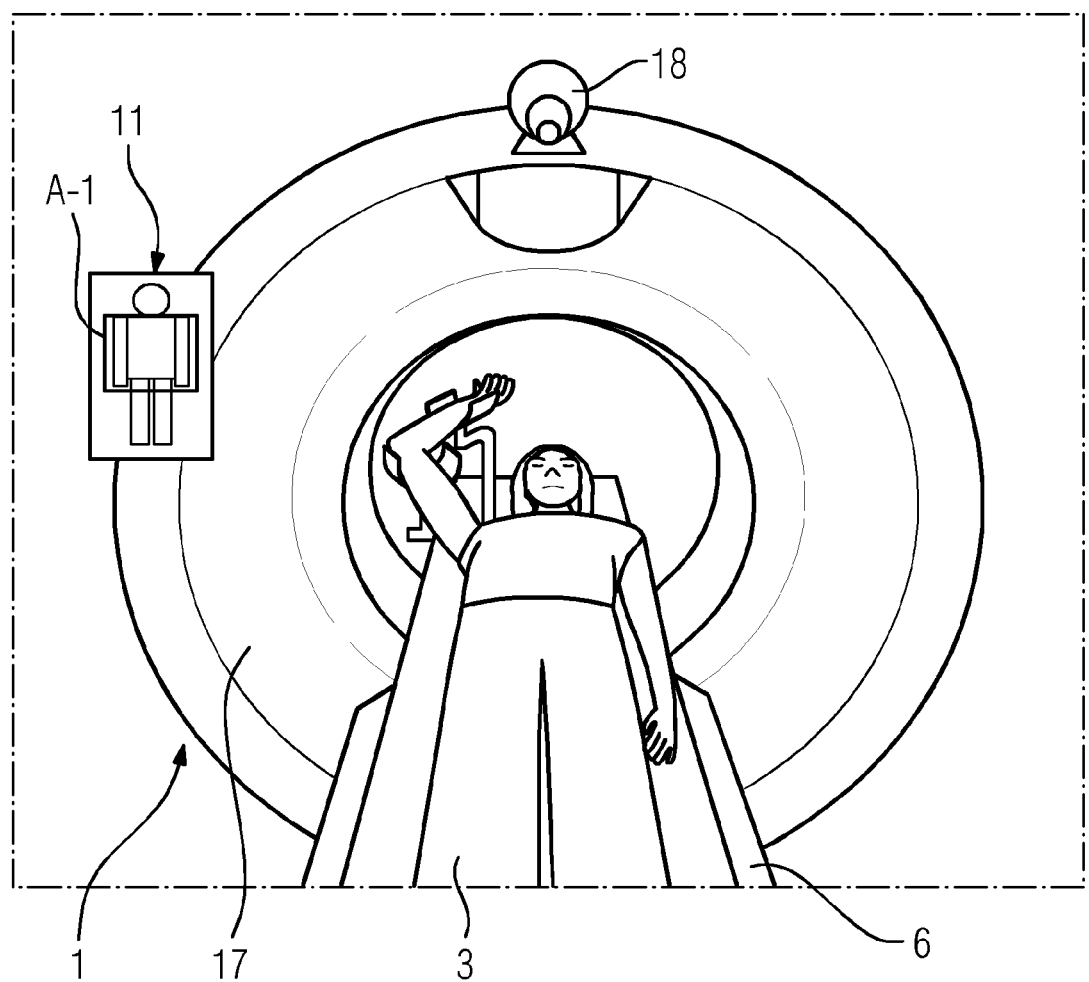
FIG. 2 The gantry of a tomography machine with a touch-sensitive screen.

FIG. 2 shows the gantry of a tomography machine together with a touch-sensitive screen. In this respect, the 3D camera 18 is aligned toward the patient table 6. Furthermore, the touch-sensitive screen 11 can be connected to the gantry 1 in a detachable manner. A connection of this type can be provided by way of a holder for a mobile touch-sensitive screen 11, also referred to as a "touch-pad". In particular, this holder can be capable of swiveling. Furthermore, the image information and also a selected first recording area A-1 are displayed in schematic form. This first recording area A-1 can be modified by the interaction of an operator with the touch-sensitive screen 11. In particular, the entire first recording area A-1 can be relocated together with the first start position S-1 and the first end position E-1. Alternatively, the first start position S-1 and the first end position E-1 can also be relocated separately from each other.

FIG. 3 shows a screen view with a first recording area. The image information displayed here is embedded into a graphical user interface and incorporates a picture 23 of the patient 3. In the example shown here, the first recording area A-1 is displayed by way of a first zone F-1 which is highlighted with respect to the surroundings. It is delimited by a first start position S-1, displayed symbolically by a solid line, and also by a first end position E-1, displayed symbolically by a dotted line. Furthermore, the recording direction is shown symbolically, by way of arrows 22 in the example shown here. Based on the selection of the first recording area A-1, a first position P-1 can now be determined automatically. Furthermore, a change-over symbol 24 is displayed. The recording direction for the first recording area A-1 can be changed by the interaction of an operator with the change-over symbol 24. In the event of a change in the recording direction, then in this case the first start position S-1 becomes the first end position E-1 and the first end position the first start position S-1. The interaction takes place via the input unit 7, that is to say by touching a touch-sensitive screen for example. Furthermore, a change-over in the recording direction can be carried out by moving the first start position S-1 relative to the first end position E-1. In this respect, the first start position S-1 moves along the system axis 5 and beyond the end position E-1.

FIG. 4 shows a screen view with a first and also a second recording area. In the example shown here, both the first recording area A-1 and also the second recording area A-2 incorporate the thorax of a patient 3. The first recording area A-1 is displayed as a first zone F-1 and the second recording area A-2 as a second zone F-2. The area where the first recording area A-1 and the second recording area A-2 overlap is displayed by way of a third zone F-3. Displaying the third zone F-3 results in the user being able to identify immediately how well the first recording area A-1 and the second recording area A-2 coincide.

In the example shown here, the recording area A-1 has been selected by inputting a first start position S-1 and also by inputting a first end position E-1 via the graphical user interface. On the other hand, the second recording area A-2, with the second start position S-2 and the second end position E-2, has been selected in this case by calling up a stored recording protocol. The recording protocol called up relates to the tomographic recording of a lung as the examination area 21. A recording protocol of this type incorporates information about a recording area for a tomographic recording of a lung. Information of this type relates in particular to the position and size of the recording area relative to the patient 3. The precision and size of the recording area can be ascertained by using landmarks 27 and/or a scalable patient model. The second recording area A-2 is therefore defined by way of the examination area 21 in the example shown here.

Furthermore, the selected examination area 21 is displayed in the image information, which area involves the lung of the patient 3. In a further embodiment, selection of the examination area 21 is carried out by way of a marking. A marking of this type can be based on the selection of a recording protocol. The marking can also be based on an input by an operator in the displayed image information via the graphical user interface. For example, the input of a marking can be carried out by using a touch-sensitive screen, by pressing a point or touching a specific area in the displayed image information. Furthermore, the marking can be carried out by placing a symbol in the displayed image information. In the example shown here, the symbol is the marking zone 25.

In one embodiment of the invention, the marking is used to select the first recording area A-1 and/or the second recording area A-2. For example, a recording area can be selected automatically around a marking. Furthermore, a selection of this type can be dependent on the position of the marking. In a further embodiment of the invention, the system is designed so as to assign the position of the marking to an area of the body of the patient 3, and to display a corresponding recording area in the image information. In the example shown here, the second recording area A-2 is displayed on the basis of the position of the marking in the form of a marking zone 25. In particular, the assignment and display can be based on the identification of anatomical landmarks 27 in the 3D image and/or in the image information. In a further embodiment, the position of the marking is set in relation to identified anatomical landmarks 27, and a recording area is derived from this relationship and displayed. In a further embodiment, the marking is carried out by the selection of the first recording area A-1 so that the first recording area A-1 specifies the marked area. Furthermore, the inputting of the marking can incorporate a confirmation stage or a correction stage. The confirmation or correction can refer both to an input identified by the system and also to a displayed recording area.

The second recording area A-2 can be selected by using a learning algorithm. In this respect, the learning algorithm is trained to select a second end position E-2, and therefore the second recording area A-2, as a function of a selected second start position S-2. In this case, the second start position S-2 can be, in particular, the first start position S-1. An operator can then select a first end position E-1 by confirming or correcting the second end position E-2. The learning algorithm is based on the finding that specific start positions are linked to specific recording areas. Furthermore, the second start position S-2 can be determined relative to an anatomical landmark 27 so that the learning algorithm analyzes the second start position relative to the anatomical landmark 27. A variant of the method described here incorporates the training of the learning algorithm, where the confirmation or correction of a second end position E-2 selected by using the learning algorithm is taken into account during a further selection of a second end position E-2.

In a further embodiment not shown here, the first recording area A-1 is compared with the second recording area A-2, wherein a confirmation signal or a warning is displayed in the user interface on the basis of the comparison. The comparison can be carried out by using the arithmetic unit 15. The confirmation signal or the warning can involve a static or dynamic signal in each case. In particular, the confirmation signal can be displayed if the first recording area A-1 and the second recording area A-2 overlap by more than a first limit value. Furthermore, the warning can be displayed if the first recording area A-1 and the second recording area A-2 overlap by less than a second limit value.

Figure 5:
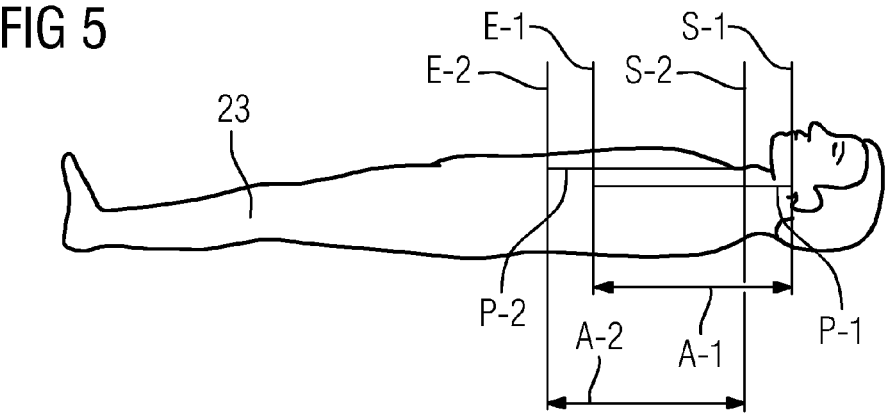

FIG. 5 shows a screen view with a first and also a second recording area in side view. This view makes it clear that the correct selection of the first recording area A-1 is important for determining CAL the first position P-1. The determination CAL of the first position P-1 takes place on the basis of the depth information and also on the basis of the selection of the first recording area A-1. Furthermore, a second position P-1 is displayed here, which is carried out on the basis of the depth information and also on the basis of the selection of the second recording area A-2. The first position P-1 constitutes the radiological central point of the first recording area A-1 and the second position P-2 the radiological central point of the second recording area A-2. In other embodiments of the invention, a geometric central point or some other central point can be involved in each case. The first position P-1 is therefore also influenced by the selection of the first recording area A-1. As a result of a more reliable selection of a recording area, the invention also enables a more reliable determination of the first, in particular vertical, position P-1 of the first recording area A-1 relative to the recording unit 17. In the embodiment of the invention shown here, the first position P-1 of the first recording area A-1 perpendicular to the system axis 5 remains constant during the recording TOM-1.

Figure 6:
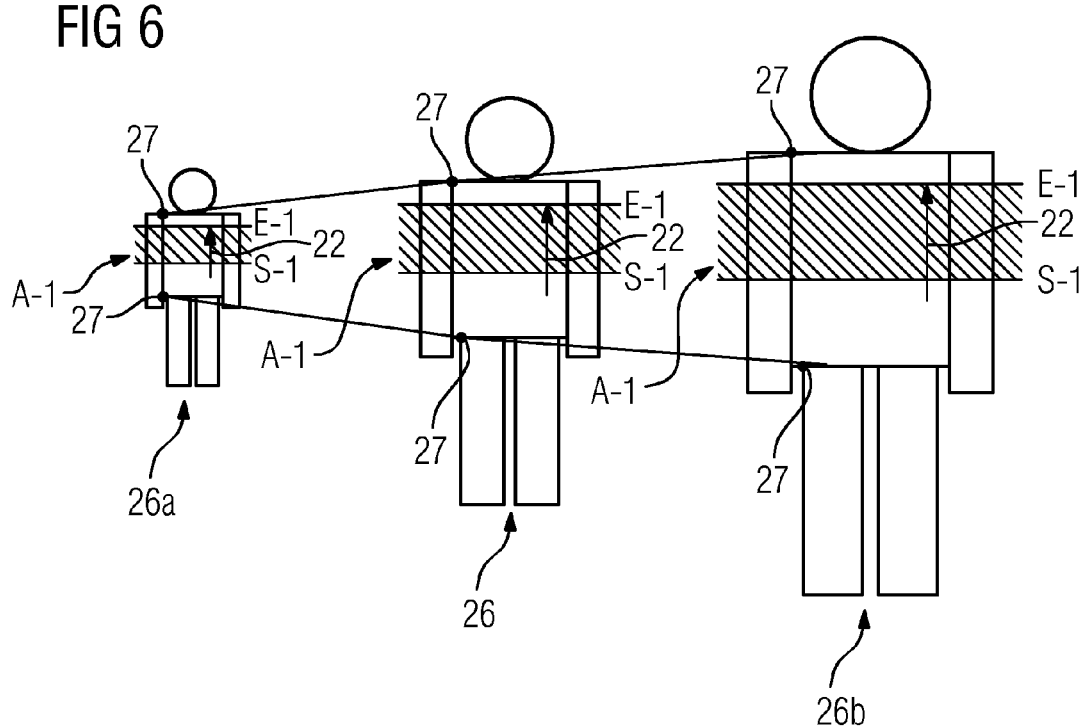

FIG. 6 shows a scalable patient model. The displayed image information can incorporate a patient model 26, for example, wherein this patient model 26 always assumes the same size on the screen 11. If a first recording area A-1 is now established, with a first start position and a first end position E-1, in the displayed image information, then the actual recording area is scaled according to the patient model. Apart from the size of individual parts of the body of the patient 3, further properties such as the size and density of organs or internal structures of the body can also be scaled in this respect. In the example shown here, the first recording area A-1 is scaled according to shoulder-hip spacing to the patient model 26a of a smaller patient and also to the patient model 26b of a larger patient. The positions of markings and/or landmarks 27 can also be scaled accordingly.

Figure 7:
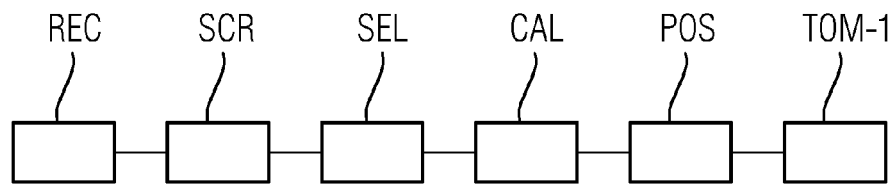

FIG. 7 shows a flow diagram for a method for selecting a recording area. An embodiment of the inventive system for selecting a recording area is structured such that it can implement an embodiment of the inventive method steps and/or activate the corresponding devices for implementing an embodiment of the inventive method.

The aforementioned description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods. Further, elements and/or features of different example embodiments may be combined with each other and/or substituted for each other within the scope of this disclosure and appended claims.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Further, at least one embodiment of the invention relates to a non-transitory computer-readable storage medium comprising electronically readable control information stored thereon, configured in such that when the storage medium is used in a controller of a magnetic resonance device, at least one embodiment of the method is carried out.

Even further, any of the aforementioned methods may be embodied in the form of a program. The program may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

None of the elements recited in the claims are intended to be a means-plus-function element within the meaning of 35 U.S.C. §112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for selecting a recording area, comprising:
receiving a 3D image of a patient supported on a patient table, wherein the 3D image incorporates depth information about an outline of the patient;
displaying image information based on the 3D image on a screen, wherein the image information is embedded into a graphical user interface;
selecting a first recording area based on the inputting of a first start position and also a first end position in the displayed image information via the graphical user interface, wherein the first recording area is displayed as a graphically highlighted first zone; and determining a first position of the first recording area relative to a recorder based on the depth information and based on the selection of the first recording area, wherein the first position specifies a geometric central point of the first recording area or of the examination area within the first recording area such that the geometric central point is situated in the isocenter of the recorder.

2. The method of claim 1, wherein the first start position and the first end position are input independently of each other.

3. The method of claim 2, wherein the image information and the graphical user interface are displayed on a touch-sensitive screen, and wherein the selection is carried out by touching the touch-sensitive screen.

4. The method of claim 2, wherein a recording direction for the first recording area is displayed symbolically in the graphical user interface, and wherein the recording direction is defined by the relative orientation of the first start position and the first end position.

5. The method of claim 2, wherein at least one examination area is marked in the image information.

6. The method of claim 1, wherein a recording direction for the first recording area is displayed symbolically in the graphical user interface, and wherein the recording direction is defined by the relative orientation of the first start position and the first end position.

7. The method of claim 1, wherein at least one examination area is marked in the image information.

8. The method of claim 1, wherein the image information and the graphical user interface are displayed on a touch-sensitive screen, and wherein the selection is carried out by touching the touch-sensitive screen.

9. A method for selecting a recording area, comprising:
receiving a 3D image of a patient supported on a patient table, wherein the 3D image incorporates depth information about an outline of the patient;
displaying image information based on the 3D image on a screen, wherein the image information is embedded into a graphical user interface;
selecting a first recording area based on the inputting of a first start position and also a first end position in the displayed image information via the graphical user interface, wherein the first recording area is displayed as a graphically highlighted first zone; and
determining a first position of the first recording area relative to a recorder based on the depth information and based on the selection of the first recording area, wherein the determining is furthermore based on an item of information about the radiation absorption of the first recording area, and wherein the first position specifies a radiological central point of the first recording area, or of the examination area within the first recording area, such that the radiological central point is situated in the isocenter of the recorder.

10. The method of claim 9, wherein the information about the radiation absorption incorporates a scalable patient model with various sub-areas, wherein the patient model is based on the 3D image and in particular the depth information, and wherein the patient model is furthermore based on generic radiation absorption properties of the sub-areas.

11. A method for selecting a recording area, comprising:
receiving a 3D image of a patient supported on a patient table, wherein the 3D image incorporates depth information about an outline of the patient;
displaying image information based on the 3D image on a screen, wherein the image information is embedded into a graphical user interface;
selecting a first recording area based on the inputting of a first start position and also a first end position in the displayed image information via the graphical user interface, wherein the first recording area is displayed as a graphically highlighted first zone; and
determining a first position of the first recording area relative to a recorder based on the depth information and based on the selection of the first recording area, wherein a second recording area with a second start position and a second end position is displayed in the image information, and wherein the second recording area is displayed as a graphically highlighted second zone.

12. The method of claim 11, wherein the second recording area is defined by way of the examination area, and wherein the examination area is selected by calling up a stored recording protocol.

13. The method of claim 11, wherein the second recording area is defined by way of the examination area, and wherein the examination area is selected by inputting a marking in the displayed image information via the graphical user interface.

14. The method of claim 11, wherein the second recording area is defined by way of the examination area, and wherein the examination area is selected at least one of in the 3D image and in the image information by way of pattern recognition.

15. The method of claim 11, wherein a graphically highlighted third zone displays the area in which the first recording area and the second recording area overlap.

16. The method of claim 11, wherein the first recording area is compared with the second recording area, and wherein a confirmation signal or a warning is displayed in the user interface on the basis of the comparison.

17. The method of claim 11, wherein the second recording area is displayed on the basis of the first start position, and wherein the first start position and the second start position coincide.

18. The method of claim 11, wherein the inputting of the first end position incorporates the confirmation or relocation of the second end position so that the first end position constitutes the confirmed or relocated second end position.

19. The method of claim 11, wherein anatomical landmarks at least one of in the 3D image and in the image information are identified by way of pattern recognition, wherein the second recording area is defined on the basis of a learning algorithm, and wherein the learning algorithm analyzes the first start position relative to the anatomical landmarks.

20. A system for selecting a recording area, comprising:
an interface to receive a 3D image of a patient supported on a patient table, wherein the 3D image incorporates depth information about the outline of the patient;
a screen to display image information based on the 3D image, wherein the image information is embedded into a graphical user interface; and
at least one processor, configured to select a first recording area based on the inputting of a first start position and also a first end position in the displayed image information via the graphical user interface, wherein the first recording area is displayed as a graphically highlighted first zone, the at least one processor being further configured to determine a first position of the first recording area relative to a recorder, with a central system axis, based on the depth information and based on the selection of the first recording area, the system being designed to implement a method for selecting a recording area, comprising:

receiving a 3D image of a patient supported on the patient table, wherein the 3D image incorporates depth information about an outline of the patient;

displaying image information based on the 3D image on a screen, wherein the image information is embedded into a graphical user interface;

selecting a first recording area based on the inputting of a first start position and also a first end position in the displayed image information via the graphical user interface, wherein the first recording area is displayed as a graphically highlighted first zone; and determining a first position of the first recording area relative to the recorder based on the depth information and based on the selection of the first recording area.

21. A system for selecting a recording area, comprising:
an interface to receive a 3D image of a patient supported on a patient table, wherein the 3D image incorporates depth information about the outline of the patient;
a screen to display image information based on the 3D image, wherein the image information is embedded into a graphical user interface;
at least one processor, configured to select a first recording area based on the inputting of a first start position and also a first end position in the displayed image information via the graphical user interface, wherein the first recording area is displayed as a graphically highlighted first zone, the at least one processor being further configured to determine a first position of the first recording area relative to a recorder, with a central system axis, based on the depth information and based on the selection of the first recording area;
a tomography machine;
the patient table being movable along the system axis; and
a radiation source and a radiation detector operating in conjunction with the radiation source,
the at least one processor being further configured to automatically position the first recording area in the first position by controlling movement of the patient table relative to the recorder, wherein the tomography machine is designed for a first recording of the first recording area in the first position.

22. The system of claim 21, wherein the screen a is a touch-sensitive screen.

23. A system for selecting a recording area, comprising:
a 3D camera, wherein the 3D camera is aligned toward a patient table;
an interface to receive a 3D image of a patient supported on the patient table, wherein the 3D image incorporates depth information about the outline of the patient;
a screen to display image information based on the 3D image, wherein the image information is embedded into a graphical user interface; and
at least one processor, configured to select a first recording area based on the inputting of a first start position and also a first end position in the displayed image information via the graphical user interface, wherein the first recording area is displayed as a graphically highlighted first zone, the at least one processor being further configured to determine a first position of the first recording area relative to a recorder, with a central system axis, based on the depth information and based on the selection of the first recording area, the system being designed to implement a method for selecting a recording area, comprising:

receiving a 3D image of a patient supported on the patient table, wherein the 3D image incorporates depth information about an outline of the patient;

displaying image information based on the 3D image on the screen, wherein the image information is embedded into a graphical user interface;

selecting a first recording area based on the inputting of a first start position and also a first end position in the displayed image information via the graphical user interface, wherein the first recording area is displayed as a graphically highlighted first zone; and determining a first position of the first recording area relative to the recorder based on the depth information and based on the selection of the first recording area.

24. A system for selecting a recording area, comprising:
a 3D camera, wherein the 3D camera is aligned toward a patient table;
an interface to receive a 3D image of a patient supported on the patient table, wherein the 3D image incorporates depth information about the outline of the patient;
a screen to display image information based on the 3D image, wherein the image information is embedded into a graphical user interface; and
at least one processor, configured to select a first recording area based on the inputting of a first start position and also a first end position in the displayed image information via the graphical user interface, wherein the first recording area is displayed as a graphically highlighted first zone, the at least one processor being further configured to determine a first position of the first recording area relative to a recorder, with a central system axis, based on the depth information and based on the selection of the first recording area;
a tomography machine;
the patient table being movable along the system axis; and
a radiation source and a radiation detector operating in conjunction with the radiation source, the at least one processor being further configured to automatically position the first recording area in the first position by controlling movement of the patient table relative to the recorder, wherein the tomography machine is designed for a first recording of the first recording area in the first position.

25. The system of claim 24, wherein the screen a is a touch-sensitive screen.

26. A method for selecting a recording area, comprising:
receiving a 3D image of a patient supported on a patient table, wherein the 3D image incorporates depth information about an outline of the patient;

displaying image information based on the 3D image on a screen, wherein the image information is embedded into a graphical user interface;

selecting a first recording area based on the inputting of a first start position and also a first end position in the displayed image information via the graphical user interface, wherein the first recording area is displayed as a graphically highlighted first zone; and determining a first position of the first recording area relative to a recorder based on the depth information and based on the selection of the first recording area, wherein the first start position and the first end position are input independently of each other and wherein the determining is furthermore based on an item of information about the radiation absorption of the first recording area, and wherein the first position specifies a radiological central point of the first recording area, or of the examination area within the first recording area, such that the radiological central point is situated in the isocenter of the recorder.

27. The method of claim 26, wherein the information about the radiation absorption incorporates a scalable patient model with various sub-areas, wherein the patient model is based on the 3D image and in particular the depth information, and wherein the patient model is furthermore based on generic radiation absorption properties of the sub-areas.

28. A system for selecting a recording area, comprising:
a display screen to receive a 3D image of a patient supported on a patient table, the 3D image incorporating depth information about an outline of the patient, and to display image information based on the 3D image;
a graphical user interface, the image information being embedded into the graphical user interface, to receive an input first start position and a first end position in the displayed image information, and to select a first recording area based on the input first start position and a first end position, wherein the first recording area is displayed as a graphically highlighted first zone; and
at least one processor to determine a first position of the first recording area relative to a recorder based on the depth information and based on the selection of the first recording area, wherein the first position specifies a geometric central point of the first recording area or of the examination area within the first recording area such that the geometric central point is situated in the isocenter of the recorder.

29. A system for selecting a recording area, comprising:
a display screen to receive a 3D image of a patient supported on a patient table, the 3D image incorporating depth information about an outline of the patient and to display image information based on the 3D image;
a graphical user interface, the image information being embedded into the graphical user interface, to receive an input first start position and a first end position in the displayed image information, and to select a first recording area based on the input first start position and a first end position, wherein the first recording area is displayed as a graphically highlighted first zone; and
at least one processor to determine a first position of the first recording area relative to a recorder based on the depth information and based on the selection of the first recording area, wherein the at least one processor is further configured to determine the first position based on an item of information about the radiation absorption of the first recording area, and wherein the first position specifies a radiological central point of the first recording area, or of the examination area within the first recording area, such that the radiological central point is situated in the isocenter of the recorder.

30. A system for selecting a recording area, comprising:
a display screen to receive a 3D image of a patient supported on a patient table, the 3D image incorporating depth information about an outline of the patient and to display image information based on the 3D image;
a graphical user interface, the image information being embedded into the graphical user interface, to receive an input first start position and a first end position in the displayed image information, and to select a first recording area based on the input first start position and a first end position, wherein the first recording area is displayed as a graphically highlighted first zone; and
at least one processor to determine a first position of the first recording area relative to a recorder based on the depth information and based on the selection of the first recording area, wherein a second recording area with a second start position and a second end position is displayed in the image information, and wherein the second recording area is displayed as a graphically highlighted second zone.

31. A system for selecting a recording area, comprising:
a display screen to receive a 3D image of a patient supported on a patient table, the 3D image incorporating depth information about an outline of the patient and to display image information based on the 3D image;
a graphical user interface, the image information being embedded into the graphical user interface, to receive an input first start position and a first end position in the displayed image information, and to select a first recording area based on the input first start position and a first end position, wherein the first recording area is displayed as a graphically highlighted first zone; and
at least one processor to determine a first position of the first recording area relative to a recorder based on the depth information and based on the selection of the first recording area, wherein the first start position and the first end position are input independently of each other and wherein the at least one processor is further configured to determine the first position based on an item of information about the radiation absorption of the first recording area, and wherein the first position specifies a radiological central point of the first recording area, or of the examination area within the first recording area, such that the radiological central point is situated in the isocenter of the recorder.

* * * * *